US006180162B1

(12) United States Patent
Shigeru et al.

(10) Patent No.: US 6,180,162 B1
(45) Date of Patent: Jan. 30, 2001

(54) METHOD OF PRODUCING ANTIMICROBIAL METAL ARTICLES AND ANTIMICROBIAL METAL ARTICLES PRODUCED BY THE METHOD

(75) Inventors: Keijiro Shigeru; Yoshitomo Inoue, both of Funabashi; Takeshi Yokota, Chiba; Misako Tochihara, Chiba; Susumu Satoh, Chiba, all of (JP)

(73) Assignees: Sumitomo Osaka Cement Co., Ltd., Tokyo; Kawasaki Steel Corporation, Hyogo, both of (JP)

(*) Notice: Under 35 U.S.C. 154(b), the term of this patent shall be extended for 0 days.

(21) Appl. No.: 09/341,177
(22) PCT Filed: Nov. 10, 1998
(86) PCT No.: PCT/JP98/05055
§ 371 Date: Jul. 6, 1999
§ 102(e) Date: Jul. 6, 1999
(87) PCT Pub. No.: WO99/25898
PCT Pub. Date: May 27, 1999

(30) Foreign Application Priority Data

Nov. 14, 1997 (JP) ...................................... 9-313429
Mar. 4, 1998 (JP) .................................. 10-051990

(51) Int. Cl.$^7$ ...................................................... B05D 7/14
(52) U.S. Cl. ........................ 427/11; 427/369; 427/2.24; 427/2.28; 427/205; 428/907
(58) Field of Search ............................. 427/11, 428, 355, 427/359, 360, 365, 369, 275, 202, 205, 2.24, 2.28; 428/907

(56) References Cited

U.S. PATENT DOCUMENTS 4,008,351 * 2/1977 Inoue et al. ......................... 428/411
4,797,231 * 1/1989 Schumanne et al. ................. 252/547
5,772,640 * 6/1998 Modak et al. ......................... 604/265
5,873,904 * 2/1999 Ragheb et al. ............................ 623/1

FOREIGN PATENT DOCUMENTS

| 5-339743 | 12/1993 | (JP) . |
| 7-228982 | 8/1995 | (JP) . |
| 8-049085 | 2/1996 | (JP) . |
| 9-104959 | 4/1997 | (JP) . |
| 9-125284 | 5/1997 | (JP) . |
| 9-131506 | 5/1997 | (JP) . |
| 9-176800 | 7/1997 | (JP) . |
| 9-201905 | 8/1997 | (JP) . |
| 9-209173 | 8/1997 | (JP) . |
| 10-259456 | 9/1998 | (JP) . |

* cited by examiner

Primary Examiner—Shrive Beck
Assistant Examiner—Jennifer Kolb
(74) Attorney, Agent, or Firm—Young & Thompson

(57) ABSTRACT

An excellent antibacterial property is afforded upon a metallic article by simple steps of coating a dispersion liquid or a solution of fine particles made of an antibacterial ingredient on the surface of the metallic article and pressing the resulting coated surface of the metallic article under a non-heated condition or rubbing the resulting coated surface of the metallic article. In addition, a conventional rolling step or the like can be used itself without any change in the above treatment, which is economically extremely advantageous. Furthermore, since the antibacterial metallic article according to the present invention is obtained under the non-heated condition, the antibacterial ingredient is not deteriorated. Further, since the antibacterial property is not lost through some abrasion, excellent antibacterial property can be exhibited over an extended time period. Further, there is no fear that surface characteristics of the metallic article, for example, a tone of color will change.

Figure 1:
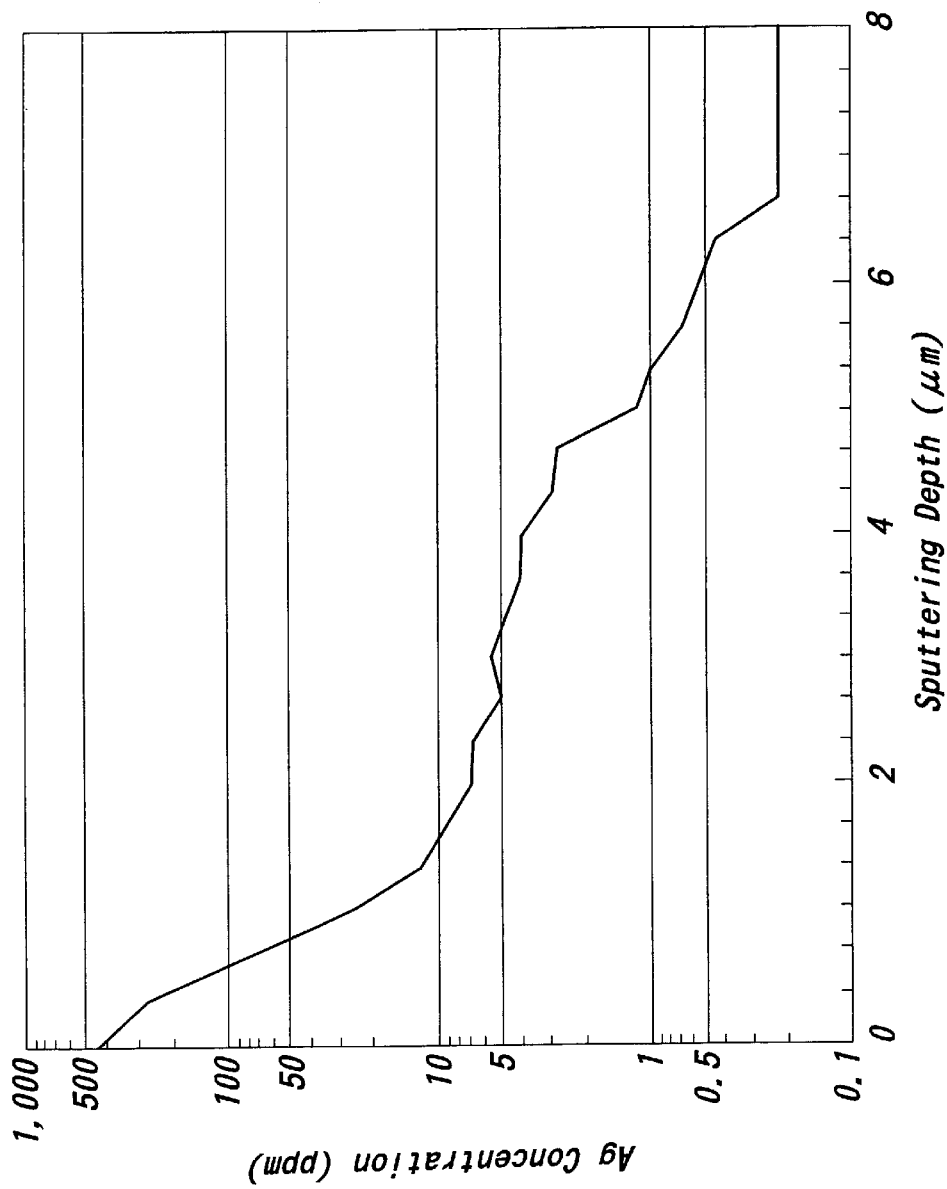

28 Claims, 1 Drawing Sheet

METHOD OF PRODUCING ANTIMICROBIAL METAL ARTICLES AND ANTIMICROBIAL METAL ARTICLES PRODUCED BY THE METHOD

TECHNICAL FIELD

The present invention relates to a method for producing an antibacterial metallic article and such an antibacterial metallic article produced by this method. Particularly, the invention is to simply and easily afford an antibacterial property upon the metallic articles at a low cost without making any change in the conventional producing process of the metallic articles.

The antibacterial property in the present invention also means anti-mildew property and anti-algae property. The metallic article generally includes articles made of metals, for example, metallic articles made of stainless steel and aluminum sheets and plates.

1. Background Techniques

Among a recent tendency of seeking hygiene and cleanliness, attention has been paid to materials upon which the antibacterial property is afforded by utilizing a metal having a so-called oligodynamic effect to suppress propagation of bacteria, molds, algae, etc. in silver, copper, etc.

It has been demanded that the antibacterial property be afforded upon every material, because toxic bacteria such as disease-causing colon bacilli-157 and MRSA have epidemically occurred. Metallic articles are not exceptional for this demand.

For example, JP-A-8 49085 proposes stainless sheet and plate having excellent antibacterial property, which have metallic layers or alloy layers of Cr, Ti, Ni or Fe containing Ag and/or Cu formed on their surfaces by magnetron sputtering, and that such a stainless sheet or plate is preferably formed with a metallic layer or an alloy layer containing 19 to 60 wt % of Ag.

JP-A-9 176800 proposes a method in which an antibacterial Austenitic stainless steel is obtained by thermally treating an Austenitic stainless steel having a composition containing C, Si, Mn, Cr, Ni and Cu in their respectively specific amounts in a temperature range of 500 to 900° C.

Besides them, JP-A-10 259,456 discloses a method in which stainless steel sheet and plate having excellent antibacterial property are obtained by incorporating 0.05 to 1.0 wt % of Ag in the stainless steel and dispersing Ag phases having minor axes of not more than 10 $\mu$m in a plane fractional percentage of not less than 0.03% in a matrix.

However, in the case of the antibacterial stainless steel sheet and plate disclosed in JP-A-8 49,085, the layer containing the antibacterial metal is peeled or removed by drawing or surface-processing, so that there is a problem that an effect thereof will not be expected.

Furthermore, in this method, since the metallic layer or the alloy layer is formed on the surface of the stainless sheet or plate, there is problems that the number of producing steps increases as compared with the conventional process, and that the surface characteristics of the stainless steel sheet or plate, for example, the tune of color is changed.

Meanwhile, in the Austenitic stainless steel disclosed in JP-A-9-176,800 and stainless steel sheet and plate disclosed in JP-A-10-259,456, the antibacterial ingredient is present uniformly up to an inner portion of the steel sheet. However, such stainless steel sheet and plate have a problem that since the antibacterial ingredient deeply existing inside the stainless steel sheet or plate does not exert any effective action upon the bacteria, mold and algae attached to the surface thereof, which is uneconomical.

2. Disclosure of the Invention

The present invention, which has been developed based on the above-mentioned present circumstances, is to solve the above economical problems by concentratedly distributing the antibacterial ingredient in the surface layer portion of the metallic article only. The present invention is aimed at proposing a method for advantageously producing the antibacterial metallic article in which the antibacterial property is not lost in a short time through penetrating the antibacterial ingredient into the metallic article by pressing, rubbing or the like, while no adverse effect is given upon the surface property thereof. The invention is also aimed at proposing the antibacterial metallic article obtained by this producing method.

That is, the gist and the construction of the present invention is as follows.

1. Method for producing the antibacterial metallic article, characterized in that a dispersion liquid or a solution of fine particles of the antibacterial ingredient is coated upon the surface of the metallic article, and the resulting coated surface is pressed under non-heated condition (First Invention).
2. Method for producing the antibacterial metallic article, characterized in that a dispersion liquid or a solution of fine particles of the antibacterial ingredient is coated upon the surface of the metallic article, and the resulting coated surface is rubbed (Second Invention).
3. The antibacterial metallic article-producing method in the above 1 or 2, wherein the antibacterial metallic article-producing method is characterized in that the antibacterial ingredient is at least one selected from the group consisting of silver, copper, a silver-copper alloy, silver chloride, silver sulfide, silver oxide, silver sulfate, silver phosphate, a silver salt of an organic acid, copper (I) chloride, copper (II) chloride, copper (I) sulfide, copper (II) sulfide, copper (I) oxide, copper (II) oxide, copper (I) sulfate, copper (II) sulfate, copper phosphate and a copper salt of an organic acid.
4. The antibacterial metallic article-producing method set forth in the above 1 or 2, wherein the concentration of the antibacterial ingredient in the dispersion liquid or the solution is 0.01 to 10 wt %.
5. The antibacterial metallic article-producing method set forth in the above 1 or 2, wherein particle diameters of the fine particles of the antibacterial ingredient are not more than 10 $\mu$m.
6. The antibacterial metallic article-producing method set forth in the above 1, wherein pressing means is rolling, hydrostatic pressing or pressing.
7. The antibacterial metallic article-producing method set forth in the above 1, wherein a pressing pressure is not less than 1 kg/mm².
8. The antibacterial metallic article-producing method set forth in the above 2, wherein rubbing means is coated surface-rubbing, grinding or polishing.
9. Antibacterial metallic article produced by the producing method set forth in above 1 or 2.

In the following, embodiments according to the present invention in more detail.

This embodiment is given to concretely illustrate the present invention so that the invention will be more understood, but the invention is not limited thereto unless otherwise specified.

In the antibacterial metallic article according to this embodiment, the antibacterial component is penetrated directly from the surface of the metal to a portion underneath the metal surface layer under the non-heated condition.

In this case, in order to penetrate the bacterial ingredient into the metallic article under the non-heated condition, it is preferable that dirt is removed from the antibacterially treated surface of the metallic article by fully washing it, coating the resulting metallic surface is coated with the dispersion liquid or the solution of the fine particles of the antibacterial ingredient (hereinafter referred to as "coating liquid"), and the antibacterial ingredient is impregnated into a portion underneath of the surface layer portion from the metallic surface by pressing the coated metallic surface upon application of pressure under the non-heated condition or by the rubbing treatment of the coated surface.

In view of the oligodynamic effect, the penetration readiness of the antibacterial ingredient into the metallic article underneath the surface layer portion, the safety and freedom from the surface characteristics of the metallic article such as the tune of color, as the antibacterial ingredient are particularly suitable silver, copper, a silver-copper alloy, silver chloride, silver sulfide, silver oxide, silver sulfate, silver phosphate, a silver salt of an organic acid, copper (I) chloride, copper (II) chloride, copper (I) sulfide, copper (II) sulfide, copper (I) oxide, copper (II) oxide, copper (I) sulfate, copper (II) sulfate, copper phosphate and a copper salt of an organic acid.

The coating liquid is obtained by dispersing or dissolving fine particles of the antibacterial ingredient in water or an organic solvent, and such a coating liquid of which wettability upon the surface of the metallic article is improved by using a soluble organic acid salt such as sodium citrate, condensed sodium phosphate, a soluble or emulsion-type organic resin, a surface active agent or the like in combination is preferred.

The coating liquid may be coated by spraying, dipping or the like, which is not particularly restrictive.

The concentration of the antibacterial ingredient is preferably 0.01 to 10 wt % or so. If the concentration is lower than this range, sufficient antibacterial property cannot be obtained. On the other hand, if it is higher than this range, dirt resulting from the antibacterial ingredient is more likely to remain.

The particle diameters of the antibacterial ingredient in the coating liquid are preferably not more than 10 $\mu$m, more preferably not more than 0.1 $\mu$m. If the antibacterial ingredient having such particle diameters is used, it is easily penetrated into the interior beneath the surface layer of the metallic article.

The penetrating depth of the antibacterial ingredient needs to be at least around 0.1 $\mu$m in view of daily treatment such as cleaning. On the other hand, no particular limitation is posed upon the penetrating depth of the antibacterial ingredient, but the penetrating depth is sufficiently around 100 $\mu$m in view of the cost, use condition of the article, etc. The penetrating depth is preferably in a range of 0.5 to 30 $\mu$m.

After the coating liquid is applied to the surface of the metallic article in the above manner, the antibacterial ingredient is impregnated into the inner portion underneath the surface layer of the metallic article by pressing under the non-heated condition or rubbing according to the first or second invention, respectively. In the following, preferred embodiments according to the present invention will be explained.

First Invention

The pressing pressure is not particularly limited. The pressing pressure is preferably not less than 1 kg/mm$^2$, particularly such that the metallic article may be slightly deformed. The pressing time period is not particularly limited, and may be a short time (in an instant). An appropriate pressing pressure varies depending upon the kind of the antibacterial ingredient used and the depth at which the antibacterial ingredient is to be penetrated.

The pressing means is not particularly limited, and for example, roll pressing, isostatic pressing or ordinary pressing may be used. Particularly, since the rolling pressing method can be employed without making any change to the existing the rolling step, this method is advantageous.

Further, the atmosphere for pressing is not particularly limited, and pressing is ordinarily effected in air.

Although a non-penetrated part of the antibacterial ingredient may remain on the surface of the metallic article after the pressing, it can be easily removed by pickling or polishing. Since the antibacterial ingredient is penetrated into a portion of the metallic article underneath the surface layer thereof, the antibacterial property is not lost or degradated even after the removal of the non-penetrated part of the antibacterial ingredient, and excellent bacterial property can be still maintained.

Second Invention

The pressing pressure in the rubbing treatment, there is no particular limitation. It is sufficient to lightly rub the coated surface of the metallic article. At this time, heating needs not be particularly effected.

The atmosphere in the rubbing is not particularly limited, but the rubbing is ordinarily effected in air.

As concrete rubbing means, mention may be made of (1) rubbing the coated surface with an object such as a cloth, a paper, a wood piece or a metallic piece, (2) grinding and (3) polishing by way of example.

The antibacterial ingredient in the coating liquid is penetrated into scratches and cracks at the surface of the metallic article and gaps in the grain boundaries of the metallic article, the coating liquid in the above-mentioned rubbing treatment. Consequently, even after the antibacterial ingredient remaining on the surface of the metallic article is removed, the antibacterial property is not lost or degraded but excellent antibacterial property is exhibited as in the first invention.

Meanwhile, it is considered that that part of the antibacterial ingredient which is exposed to the surface of the metallic article exhibits the antibacterial property of the antibacterial metallic article. Therefore, if the surface of the metallic article is worn or corroded, the inner antibacterial ingredient is newly exposed to prevent degradation of the antibacterial property.

Further, since neither metallic layer nor alloy layer is formed on the surface of the metallic article, the surface characteristics of the metallic article, for example, a tone of color do not change.

Furthermore, since the antibacterial ingredient is penetrated into the metallic article under the non-heated condition, the antibacterial ingredient is not degraded, so that the excellent antibacterial ingredient can be not only maintained, but also less limitation is posed upon the production.

The metallic article is not particularly limited, and sheets and plates such as stainless steel sheets and plates, iron steel sheets and plates, aluminum sheets and plates, and copper sheets and plates as well as other metallic articles having arbitrary shapes may be recited.

In the first invention, the roll pressing method can be used as the pressing means. Since this rolling pressing method does not require any change upon the existing rolling step, the present invention is favorably applied to the roll pressing step, when the metallic article is of a sheet-like or plate-like shape.

On the other hand, the production of the metallic article includes a polishing or a grinding step. An infinite number of scratches, cracks and the like exist in the surfaces of the metallic articles having undergone such a step. Further, an infinite number of grain boundaries exist in the metallic articles made of a polycrystal such as stainless steel. Therefore, if the second invention is applied to the polishing or grinding step, the antibacterial metallic articles can be easily obtained as in the above case without making any change to the existing step.

As mentioned above, according to the present invention, the antibacterial ingredient can be easily and effectively permeated into a portion of the metallic article under the surface layer, and such a penetrated ingredient can be stably held for a long time period without being lost in a short time period. Therefore, excellent antibacterial property can be exhibited over an extended time period.

BRIEF DESCRIPTION OF THE INVENTION

FIG. 1 is a graph showing the concentration and the penetrated depth of the antibacterial ingredient in a surface layer portion of the metallic article.

BEST MODE FOR CARRYING OUT THE INVENTION

EXAMPLE 1

An aqueous dispersion liquid of fine silver particles having the average particle diameter of 20 nm (0.02 $\mu$m) prepared by a conventional method is applied to a SUS 430 stainless steel sheet in an amount of 0.1 g/m$^2$ by using a roll coater.

The silver was penetrated into a portion inside a surface layer of the stainless steel sheet under application of a pressing pressure of 10 kg/mm$^2$ (temperature: 25° C.) upon the coated surface with use of a rolling roll.

Then, the antibacterial stainless steel sheet was obtained by pickling with a 5% aqueous solution of nitric acid.

The penetrated state of the silver in the surface layer portion of this antibacterial stainless steel sheet was analyzed by a GDMS method (glow discharge mass spectrometry), which confirmed that as shown in FIG. 1, about 400 ppm silver atoms existed at the surface and that silver atoms existed at a depth of up to about 6 $\mu$m. Therefore, the antibacterial property will not be lost by slight wearing.

With respect to the thus produced antibacterial stainless sheet, an antibacterial test (test bacteria: *Escherichia coli* and *Staphylococcus aureus*) was then effected according to "Film adhering method" specified by Antibacterial Product Technology Association, and results were evaluated.

Results obtained are shown in Table 1.

The film adhering method is outlined as follows:

To a test sample was inoculated 0.5 ml/25 cm$^2$ of a bacteria liquid of *Escherichia coli* and *Staphylococcus aureus* formulated at a bacteria concentration of about 10$^5$ cfu/ml and containing ordinary broth diluted at 1/500, and a polyethylene film having the same shape as that of the test sample is placed on the bacteria liquid. Then, the bacteria liquid is cultivated at a temperature of 35° C. for 24 hours, and the number of living bacteria is measured according to an agar plate method.

EXAMPLE 2

An antibacterial aluminum sheet was obtained by the same treatment as in Example 1 except that an aluminum sheet was used instead of the stainless steel sheet.

The penetrated state of silver in a surface layer portion of this antibacterial aluminum sheet was analyzed by the GDMS method, which confirmed that about 500 ppm silver atoms existed at the surface and that silver atoms existed at a depth of up to about 10 $\mu$m.

Then, the antibacterial property of the thus produced antibacterial aluminum sheet was evaluated according to Example 1.

Results obtained are also shown in Table 1.

EXAMPLE 3

An antibacterial stainless steel was obtained by the same treatment as in Example 1 except that a dispersion liquid of fine silver particles having the average particle diameter of 100 nm (0.1 $\mu$m) produced by a conventional method was used.

The penetrated state of copper in a surface layer portion of this antibacterial stainless sheet was analyzed by the GDMS method, which confirmed that about 350 ppm copper atoms existed at the surface and that copper atoms existed at a depth of up to about 8 $\mu$m.

Then, the antibacterial property of the thus produced antibacterial stainless steel sheet was evaluated according to Example 1.

Results obtained are also shown in Table 1.

Comparative Example 1

The antibacterial property of a SUS 430 steel sheet having not undergone an antibacterial treatment was evaluated according to Example 1.

Results obtained are also shown in Table 1.

Comparative Example 2

The antibacterial property of an aluminum sheet as used in Example 2 having not undergone an antibacterial treatment was evaluated according to Example 1.

Results obtained are also shown in Table 1.

TABLE 1

| | | Number of living bacteria (cfu/ml) | |
| --- | --- | --- | --- |
| | Kind of bacterial | At the time of starting the antibacterial test | 24 hours after the anti- bacterial test |
| Example 1 | Escherichia coli | 7.1 × 10$^5$ | 5> |
| | Staphylococcus aureus | 8.3 × 10$^5$ | 5> |
| Example 2 | Escherichia coli | 6.8 × 10$^5$ | 5> |
| | Staphylococcus aureus | 6.9 × 10$^5$ | 5> |
| Example 3 | Escherichia coli | 7.1 × 10$^5$ | 5> |
| | Staphylococcus aureus | 7.9 × 10$^5$ | 5> |
| Comparative Example 1 | Escherichia coli | 7.2 × 10$^5$ | 1.4 × 10$^6$ |
| | Staphylococcus aureus | 8.3 × 10$^5$ | 4.5 × 10$^5$ |
| Comparative Example 2 | Escherichia coli | 7.1 × 10$^5$ | 1.3 × 10$^6$ |
| | Staphylococcus aureus | 8.0 × 10$^5$ | 4.1 × 10$^5$ |

As is clear from Table 1, the number of the living bacteria was less than 5 for all the metallic articles having undergone the antibacterial treatment in Examples 1 to 3, which confirmed that they were clearly different from the sheets having not undergone the antibacterial treatment in Comparative Examples 1 and 2.

In the following, two kinds of coating liquids mentioned below were used as the antibacterial coating liquid in Examples 4 to 8.

(1) Antibacterial coating liquid A

Fine metallic silver particles were obtained by reducing silver citrate with ferrous sulfate, which were filtered and washed. A composition as shown below were formulated by mixing the fine silver particles and raw materials.

| | |
|---|---|
| Fine metallic silver particles having the average particle diameter of 20 nm | 0.1 wt % |
| Sodium citrate | 0.1 wt % |
| Nonionic surface active agent | 0.3 wt % |
| Water | balance |

(2) Antibacterial coating liquid B

A composition as shown below were formulated by mixing copper sulfate and raw materials.

| | |
|---|---|
| $Cu^{2+}$ | 0.1 wt % |
| Sodium citrate | 0.1 wt % |
| Nonionic surface active agent | 0.3 wt % |
| Water | balance |

EXAMPLE 4

The above antibacterial coating liquid A was applied to a surface of a SUS 430 stainless steel sheet (coated amount: 10 $g/m^2$). After drying, the dried coated surface was polished with a hemp cloth which was impregnated with a No. 400 polishing powder (SiC powder #400: JIS R 6001, 1987), thereby obtaining an antibacterial stainless steel sheet.

Washing the surface of this antibacterial stainless steel sheet with a neutral detergent revealed that its outer appearance did not differ at all as compared with the surface before the treatment.

Further, observation of the washed surface of the stainless steel sheet with a scanning type electron microscope and an EDMA confirmed that silver entered scratches, cracks, and gaps in grain boundaries, etc. at the surface of the stainless steel sheet.

Further, analysis of the washed surface of the stainless steel sheet with the glow discharge mass spectrometry (GDMS) confirmed that silver penetrated at a dept of up to 10 $\mu$m.

EXAMPLE 5

An antibacterial stainless steel sheet was obtained by the same treatment as in Example 4 except that the above antibacterial coating liquid B was used. Washing the surface of this antibacterial stainless steel sheet in the same manner revealed that its outer appearance did not differ at all as compared with the surface before the treatment.

Further, observation of the washed surface of the stainless steel sheet in the same manner as in Example 4 confirmed that copper entered scratches, cracks, and gaps in grain boundaries, etc. at the surface of the stainless steel sheet.

Further, analysis of the washed surface of the stainless steel sheet in the same manner as in Example 4 confirmed that copper penetrated at a dept of up to 8 $\mu$m.

EXAMPLE 6

A surface of a SUS 430 stainless steel sheet was polished with a No. 180 polishing paper (SiC #180: JIS R 6001, 1987). Then, while the above antibacterial coating liquid A was being sprayed onto the polished surface (coated amount: 3 $g/m^2$), the surface was polished with a No. 320 polishing paper (SiC#320: JIS R6001, 1987). Immediately after the polishing, the stainless steel sheet was alkali-dewaxed and washed, thereby obtaining an antibacterial stainless steel sheet.

The appearance of the surface of the antibacterial stainless steel sheet did not differ at all as compared with the surface of a stainless steel sheet having polished by the No. 320 polishing paper with no antibacterial treatment.

Further, observation of the washed surface of the stainless steel sheet in the same manner as in Example 4 confirmed that copper entered scratches, cracks, and gaps in grain boundaries, etc. at the surface of the stainless steel sheet.

Furthermore, analysis of the washed surface of the stainless steel sheet in the same manner as in Example 4 confirmed that silver penetrated at a dept of up to 9 $\mu$m.

EXAMPLE 7

An antibacterial stainless steel sheet was obtained by the same treatment as in Example 6 except that the above antibacterial coating liquid B was used. It was recognized that the appearance of the surface of the antibacterial stainless steel sheet did not differ at all as compared with the surface of a stainless steel sheet having polished by the No. 320 polishing paper with no antibacterial treatment.

Further, observation of the washed surface of the stainless steel sheet in the same manner as in Example 4 confirmed that copper entered scratches, cracks, and gaps in grain boundaries, etc. at the surface of the stainless steel sheet.

Furthermore, analysis of the washed surface of the stainless steel sheet in the same manner as in Example 4 confirmed that copper penetrated at a dept of up to 5 $\mu$m.

EXAMPLE 8

The antibacterial coating liquid A was coated onto the surface of a SUS 430 stainless steel sheet by dipping it into the antibacterial coating liquid A (coated amount: 3 $g/m^2$). The coated surface was rubbed with a gauze without being dried, and was washed with pure water before the antibacterial coating liquid was dried up, thereby obtaining an antibacterial stainless steel sheet.

It was recognized that the appearance of the surface of the antibacterial stainless steel sheet did not differ at all as compared with the surface of the stainless steel before the treatment.

Further, observation of the washed surface of the stainless steel sheet in the same manner as in Example 4 confirmed that silver entered scratches, cracks, and gaps in grain boundaries, etc. at the surface of the stainless steel sheet.

Furthermore, analysis of the washed surface of the stainless steel sheet in the same manner as in Example 4 confirmed that silver penetrated at a dept of up to 3 $\mu$m.

With respect to the articles having undergone the antibacterial treatment or those having not undergone such a treatment, the antibacterial test was effected by the above-mentioned "Film adhering method", and results were evaluated.

Results obtained are shown in Table 2.

TABLE 2

| | | Number of living bacteria (cfu/ml) | |
|---|---|---|---|
| Test sample | Kind of bacteria | Before the test | 24 hours later |
| Example 4 | *Escherichia coli* | $3.7 \times 10^5$ | 5> |
| | *Staphylococcus aureus* | $4.4 \times 10^5$ | 5> |
| Example 5 | *Escherichia coli* | $3.7 \times 10^5$ | 5> |
| | *Staphylococcus aureus* | $4.4 \times 10^5$ | 5> |
| Example 6 | *Escherichia coli* | $3.7 \times 10^5$ | 5> |
| | *Staphylococcus aureus* | $4.4 \times 10^5$ | 5> |
| Example 7 | *Escherichia coli* | $3.7 \times 10^5$ | 5> |
| | *Staphylococcus aureus* | $4.4 \times 10^5$ | 5> |
| Example 8 | *Escherichia coli* | $3.7 \times 10^5$ | 5> |
| | *Staphylococcus aureus* | $4.4 \times 10^5$ | 5> |
| not treated | *Escherichia coli* | $3.7 \times 10^5$ | $2.6 \times 10^6$ |
| | *Staphylococcus aureus* | $4.4 \times 10^5$ | $6.3 \times 10^5$ |

As is clear from Table 2, the number of the living bacteria was less than 5 for all the metallic articles having undergone the antibacterial treatment in Examples 4 to 8, which confirmed that their antibacterial property was largely enhanced as compared with the sheets having not undergone the antibacterial treatment.

Industrially Applicability

According to the antibacterial metallic article-producing method of the present invention, an excellent antibacterial property can be afforded upon the metallic article merely by pressing or rubbing the surface of the metallic article to which the dispersion liquid or solution of the fine particles of the antibacterial ingredient has been applied. In addition, such a treatment is extremely simple and easy, and the conventional rolling step, etc. can be used, without any change, as they are. Therefore, the metallic article having excellent antibacterial property can be easily produced.

Further, since the antibacterial metallic article according to the present invention is obtained under the non-heated condition, the antibacterial ingredient is not degraded. Further, the antibacterial property is not lost due to some wearing, etc. Therefore, excellent antibacterial property can be exhibited for a long time period, and the surface characteristics of the metallic article, such as tone of color, do not change.

What is claimed is:

1. A method for producing an antibacterial metallic article, comprising the steps of coating a liquid composition comprising fine particles made of an antibacterial ingredient on a surface of a metallic article, and pressing the resulting coated surface of the metallic article under a non-heated condition, whereby the antibacterial ingredient is penetrated from the surface of the metallic article into a portion underneath the metal surface layer.

2. The antibacterial metallic article-producing method set forth in claim 1, wherein the antibacterial ingredient is at least one selected from the group consisting of silver, copper, a silver-copper alloy, silver chloride, silver sulfide, silver oxide, silver sulfate, silver phosphate, a silver salt of an organic acid, copper (I) chloride, copper (II) chloride, copper (I) sulfide, copper (II) sulfide, copper (I) oxide, copper (II) oxide, copper (I) sulfate, copper (II) sulfate, copper phosphate and a copper salt of an organic acid.

3. The antibacterial metallic article-producing method set forth in claim 1, wherein the concentration of the antibacterial ingredient in the liquid composition is 0.01 to 10 wt %.

4. The antibacterial metallic article-producing method set forth in claim 1, wherein particle diameters of the fine particles of the antibacterial ingredient are not more than 10 μm.

5. The antibacterial metallic article-producing method set forth in claim 1, wherein a pressing pressure is not less than 1 kg/mm².

6. An actibacterial metallic article produced by the producing method set forth in claim 1.

7. A method for producing an antibacterial metallic article, comprising the steps of coating a liquid composition comprising fine particles made of an antibacterial ingredient on a surface of a metallic article, and rubbing the resulting coated surface of the metallic article under non-heated condition, whereby the antibacterial ingredient is penetrated from the surface of the metallic article into a portion underneath the metal surface layer.

8. The antibacterial metallic article-producing method set forth in claim 7, wherein the rubbing step includes polishing.

9. The antibacterial metallic article-producing method set forth in claim 7, wherein the antibacterial ingredient is at least one selected from the group consisting of silver, copper, a silver-copper alloy, silver chloride, silver sulfide, silver oxide, silver sulfate, silver phosphate, a silver salt of an organic acid, copper (I) chloride, copper (II) chloride, copper (I) sulfide, copper (II) sulfide, copper (I) oxide, copper (II) oxide, copper (I) sulfate, copper (II) sulfate, copper phosphate and a copper salt of an organic acid.

10. The antibacterial metallic article-producing method set forth in claim 7, wherein the concentration of the antibacterial ingredient in the liquid composition 0.01 to 10 wt %.

11. The antibacterial metallic article-producing method set forth in claim 7, wherein particle diameters of the fine particles of the antibacterial ingredient are not more than 10 μm.

12. An antibacterial metallic article produced by the producing method set forth in claim 7.

13. The antibacterial metallic article-producing method set forth in claim 7, wherein the rubbing step includes grinding.

14. The method of claim 7, wherein the rubbing step is performed using a cloth.

15. The method of claim 14, wherein the cloth is impregnated with polishing powder.

16. The method of claim 14, wherein the cloth is a hemp cloth.

17. The method of claim 16, wherein the cloth is impregnated with polishing powder.

18. The method of claim 14, wherein the liquid composition comprises metallic silver particles, sodium citrate, and a nonionic surface active agent.

19. The method of claim 18, wherein the metallic silver particles have an average particle diameter of 20 nm.

20. The method of claim 19, wherein the liquid composition is applied in an amount of 10 g/m².

21. The method of claim 14, wherein the liquid composition comprises $Cu^{2+}$, sodium citrate, and a nonionic surface active agent.

22. The method of claim 7, wherein the rubbing step is performed using paper.

23. The method of claim 7, wherein the rubbing step is performed using wood.

24. The method of claim 7, wherein the rubbing step is performed using a metallic piece.

25. The method of claim 7, wherein the rubbing step is performed after the coated surface has dried.

26. A method for producing an antibacterial metallic article, comprising the steps of:

polishing a surface of the metallic article using a first polishing paper; and polishing the surface of the metallic article using a second polishing paper different from the first polishing paper while applying to the surface of a metallic article a liquid composition comprising fine particles made of an antibacterial ingredient;

wherein the polishing step using the second polishing paper is performed until the antibacterial ingredient is penetrated from the surface of the metallic article into a portion underneath the metal surface layer.

27. The method of claim 26, wherein the first polishing paper is a No. 180 polishing paper.

28. The method of claim 27, wherein the second polishing paper is a No. 320 polishing paper.

* * * * *